United States Patent [19]

Singleton

[11] Patent Number: 4,677,425
[45] Date of Patent: Jun. 30, 1987

[54] APPARATUS FOR DETECTING METAL DEBRIS PARTICLES

[75] Inventor: Donald W. Singleton, Chester, United Kingdom

[73] Assignee: Shell Oil Company, Houston, Tex.

[21] Appl. No.: 720,790

[22] Filed: Apr. 8, 1985

[30] Foreign Application Priority Data

Apr. 17, 1984 [GB] United Kingdom ............... 8409900

[51] Int. Cl.⁴ ............................................. G08B 21/00
[52] U.S. Cl. ............................... 340/627; 200/61.09; 340/631; 174/117 M
[58] Field of Search ....................... 340/607, 627, 631; 174/117 PC, 117 M; 200/61.09; 361/416

[56] References Cited

U.S. PATENT DOCUMENTS 3,824,433  7/1974  Newton, Jr. ................. 361/416
3,878,103  4/1975  Miller et al. ................. 340/627
4,030,028  6/1977  Allender .................. 340/631 X Primary Examiner—Glen R. Swann, III
Assistant Examiner—Jeffery A. Hofsass

[57] ABSTRACT

An apparatus is provided for detecting metal debris particles in a fluid flowing in machinery. The apparatus is adapted to be installed in machinery and has a grid means of electrically insulating material provided with openings of a first type and a second type respectively to allow fluid passage therethrough. Each opening is conductively connected to electric means adapted to provide an electric signal when a conducting particle of metal debris having a predetermined size is trapped in or across any of the openings.

13 Claims, 5 Drawing Figures

APPARATUS FOR DETECTING METAL DEBRIS PARTICLES

BACKGROUND OF THE INVENTION

This invention relates to an apparatus for detecting metal debris particles in a fluid flowing in machinery, for example a lubricant oil system in rotating or reciprocating machinery.

Investigations have shown that in machinery, for example rotating and reciprocating machinery such as engines, turbines, pumps, gearboxes, compressors and the like, when abnormal conditions develop in oil wetted components, the amount and size of oil transported metallic debris increases.

The early detection of these changes is essential in the prevention of rapid machine degradation and/or unscheduled stoppages resulting from machine or component failure.

Various techniques to detect circulating metal debris particles have been investigated. One of these known techniques is the use of the commercially produced "Grid Switch" particle detector as described in U.K. Patent Specification No. 1,256,291. This detector is a simple device for detecting large metal debris particles circulating in lubricant systems. Oil flows continuously through a perforated element or grid covered with a printed circuit comprising two interposed electrically conductive strips, which communicate with a relay. When a particle or particles of metal debris large enough to bridge the gap between two strips is/are trapped on the element, the relay operates and may trigger an alarm system or switch off the machinery. When an alarm is triggered the grid can be observed visually, if desired.

However, this known device is a single switch which once activated will not respond to other particles bridging the gaps between the two strips. Further, this known device is restricted to the detection of debris in oil only.

These and other limitations and disadvantages of the prior art are overcome by the present invention however, and an improved apparatus for detecting metal particles in a fluid is provided.

SUMMARY OF THE INVENTION

It is therefore an object of the invention to provide an apparatus for detecting metal debris particles in a fluid, which can respond to a plurality of particles, either individually or collectively.

It is another object of the invention to provide a device for detecting metal debris particles in a fluid, which is adapted to inform an operator of the size, quantity and the severity of contamination.

It is still another object of the invention to provide an apparatus for detecting any debris, in any fluid flowing in machinery, whether or not that fluid is oil. For example, the apparatus of the invention can be used in hydraulic systems or injection systems such as water injection systems. The invention can also be used for control fluids, for example 95 percent water based fluids.

The invention therefore provides an apparatus for detecting metal debris particles in a fluid flowing in machinery. In a preferred embodiment this apparatus is adapted to be installed in machinery and comprises a grid means of electrically insulating material provided with openings of a first type and a second type respectively to allow fluid passage and each opening being connected conductively to electric means adapted to provide an electric signal when a conducting particle of metal debris having a determined size is trapped in or across any of the openings, and wherein one side of the said grid means is provided with a plurality of first electrically conductive means and a plurality of second electrically conductive means, arranged in such a way that at the periphery of each opening of the first type two sensing contacts are provided, adapted to respond to metal debris particles, and wherein said second electrically conductive means through said openings of the second type are connected electrically to third electrically conductive means arranged on the reverse side of the grid means.

These and other objects and advantages of the present invention will become apparent from the following detailed description, wherein reference is made to the Figures in the accompanying drawings.

DETAILED DESCRIPTION OF PREFERRED EMBODIMENTS

Figure 1:
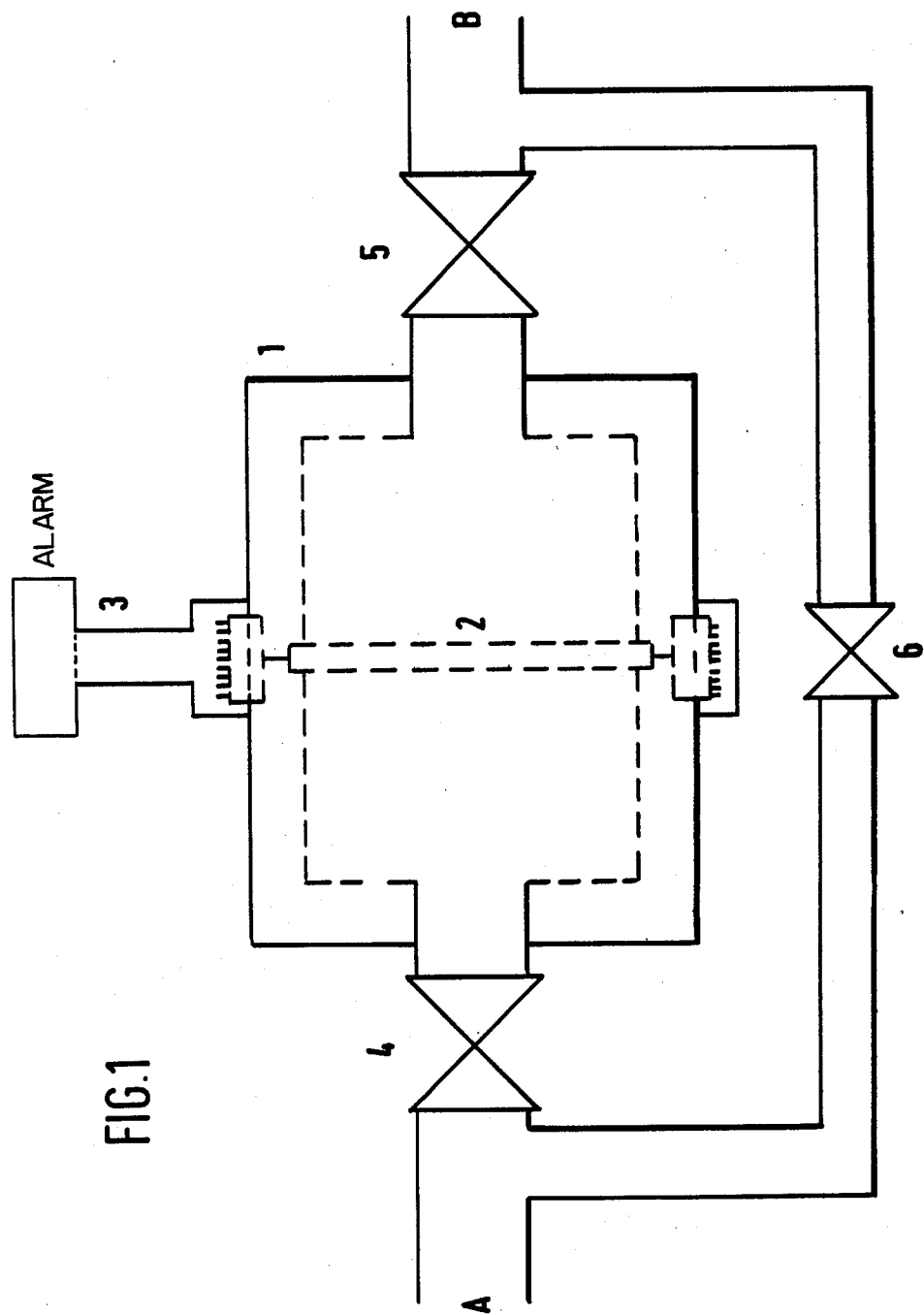
FIG. 1 represents schematically the mounting of a particle detector in machinery; in this example a lubricant oil system in rotating machinery.

Referring now to FIG. 1 there may be seen a detector housing 1 having in its interior a grid means 2 of electrically insulating material (schematically shown) which is mounted in any suitable way in machinery, for example an oil lubricant system of rotating machinery. For reasons of clarity only part of a typical lubricant system has been shown. Fluid, in this example oil is flowing continuously from the discharge A of a pump or any other pressurizing means suitable for the purpose (not shown) to the detector housing 1, passes through the grid means 2 and flows to an oil sump B (not shown). The housing 1 is provided with a suitable conduit 3 for electric connections (not shown) to the grid means. The grid means can be mounted in the housing 1 in any way suitable for the purpose.

Continuing to refer to FIG. 1, an inlet guard valve 4 and an exit guard valve 5 have been shown.

The detector housing may be installed at any suitable place in the lubricant pipework. In an advantageous embodiment the detector housing is installed on the return line from the equipment upstream of an oil filter. The basic requirements are that the grid means of the detector housing is mounted perpendicular to the flow direction of the oil and that the housing 1 itself is easily accessible.

Ideally, all the oil should flow through the grid means. However, in systems with very large oil flow rates a bypass system is required, for example a bleed valve 6 as also depicted in FIG. 1. In an advantageous embodiment the grid means and guard valves can be installed in the bypass system and not in the flow line.

Such an arrangement has several advantages; for example, there is no need to stop machinery to examine the nature of the particles.

Figure 2A:
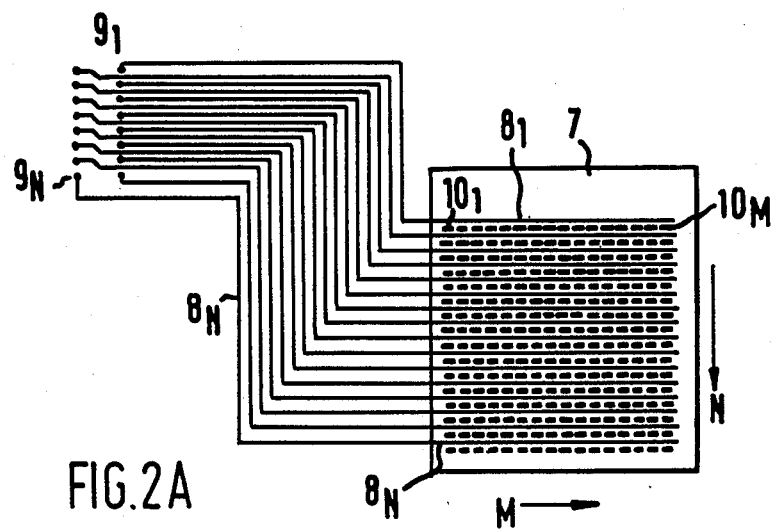
FIG. 2A represents schematically the electrically conductive means of a first side (operating side) of a grid means of the particle detector according to the invention.

Referring now to FIG. 2A a first side of grid means 2 is depicted. Perforated wafer element 7 comprises openings of a first type and a second type for fluid passage, (not shown, for reasons of clarity). The openings of the said first type and second type will be described in more detail hereinafter with reference to FIGS. 3A and 3B.

The first side of the perforated wafer element 7 has been provided with a plurality of first electrically conductive spaced means $8_1 \ldots 8_N$, which are connected in any way suitable for the purpose to output conductors $9_1 \ldots 9_N$ respectively. This example illustrates N=16, but no limitation is intended on the scope of the invention as illustrated by this or any other example herein.

The output conductors are connected in any way suitable for the purpose to a relay which may activate an alarm or switch off machinery in order to avoid damage to the machinery. For reasons of clarity the relay, alarm and possible further (electrical) circuits have not been represented.

The said first side of the said wafer element 7 has also been provided with a plurality of second electrically conductive means $10_i$ (i=1 . . . M), for example, arranged in spaced rows. Again for this example, the number of rows is 16 and M=16.

However, it will be appreciated that any value of N, M suitable for the purpose may be used and that N may or may not be equal to M.

The electrically conductive means $10_i$ are connected electrically through openings of the second type to third electrically conductive means arranged on the other side of the wafer 7. This will be described with reference to FIG. 2B.

Figure 2B:
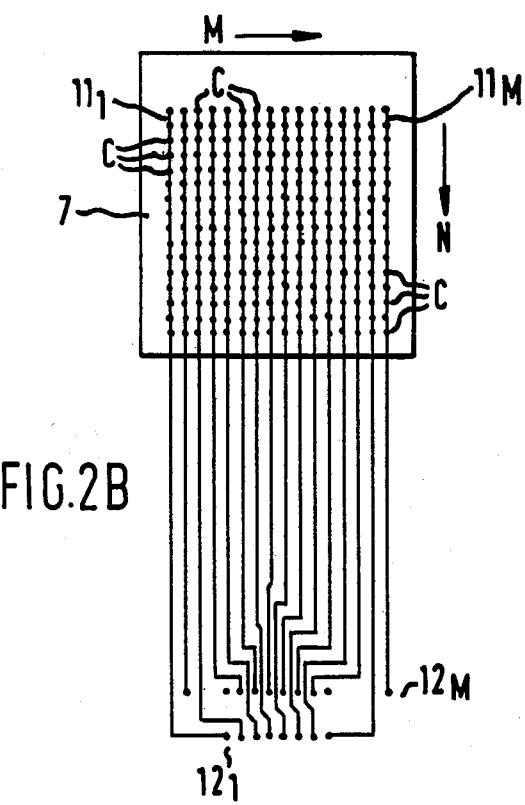
FIG. 2B represents schematically the electrically conductive means of a second side of the grid means of the particle detector of the invention, said second side being the opposite side of the said first side.

FIG. 2B represents schematically the said other side of the wafer 7. This side is provided with third electrically conductive spaced means $11_1 \ldots 11_M$ which are arranged orthogonally with respect to the first spaced means and the rows of the conductive second means represented in FIG. 2A.

These third electrically conductive means $11_i$ (i=1 . . . M) are connected in any way suitable for the purpose to output connectors $12_i$ (i=1 . . . M) which may be connected to the relay and alarm as described with reference to FIG. 2A.

Each row of third electrically conductive means $11_i$ (i=1 . . . M) comprises openings of the second type C which are connected electrically to the second electrically conductive means arranged on the said first side of the wafer and which will be described in more detail with reference to FIGS. 3A and 3B.

Figure 3A:
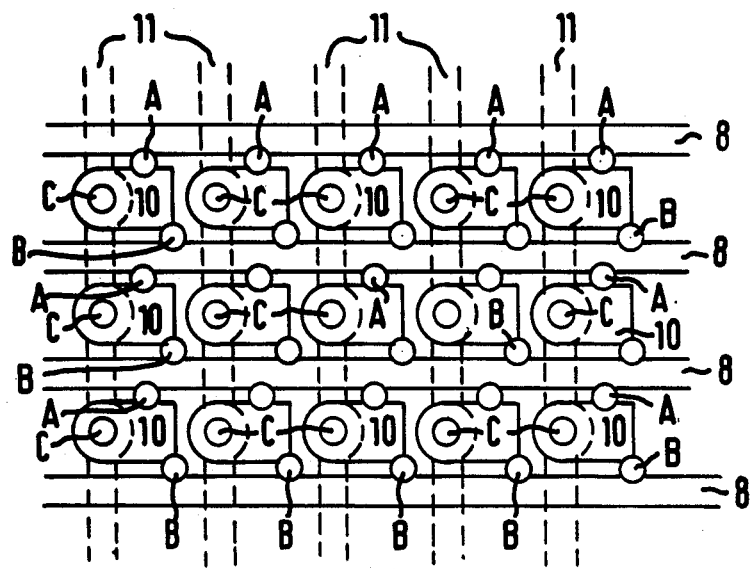
FIGS. 3A and 3B represent details of FIGS. 2A and 2B respectively.

FIG. 3A represents a detail of the first side of the grid means of FIG. 2A. The grid means comprises a plurality of first electrically conductive spaced means 8 and a plurality of second electrically conductive means 10 arranged in spaced rows. For reasons of clarity only four spaced rows of first means 8 and three rows of second means 10 have been represented. In an advantageous embodiment the said first means are strip contacts, in particular copper tracks, and the said second means are pads.

The grid means comprises a plurality of openings A, B and C. Spaced rows of unplated openings A and B of the first type adapted for the passage of fluid and the detection of metal particles are represented. The electrically conductive means (8, 10) and the openings (A, B) are arranged in such a way that at the periphery of each opening two sensing contacts are provided.

Openings of the second type C, also allow passage of fluid and are through-plated and provide electrical connections between the pads 10 on the first side of the wafer and a plurality of spaced third electrically conductive means 11 arranged in spaced rows orthogonally with respect to the rows on the first side of the wafer on the reverse side of the wafer 7. In this embodiment the said third means 11 consist of connecting strips which are shown as dashed lines in FIG. 3A. For reasons of clarity only five such connecting strips have been represented.

For reasons of clarity the further electrical connections of the respective first and third means to a possible relay and alarm have not been represented. Each first means (8) and second means (10) may form a separate switch device.

Figure 3B:
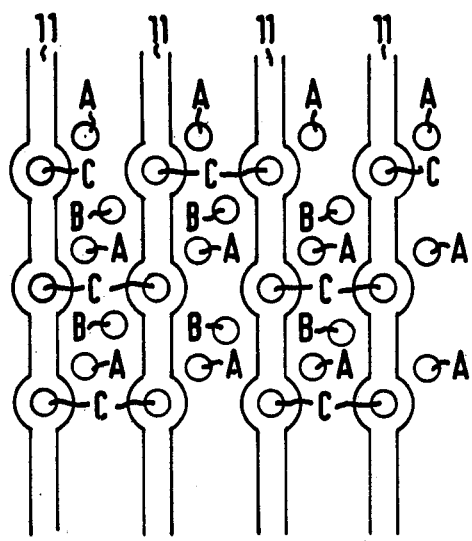

FIG. 3B represents a detail of the reverse side of FIG. 3A. The same reference numerals as in FIG. 3A have been used. Connecting strips 11 and openings A, B, C have been represented.

The operation of the device of the invention is as described hereinbelow. Any metal debris particle in the fluid, or any number of particles, which is trapped on the wafer element 7 and which is sufficiently large to bridge across two sensing contacts formed by the first and second electrically conductive means arranged on the first side of the wafer, will activate a switch and provide an alarm.

The shape and lay out of the pads and strips is not critical and can be altered to suit any application; similarly the number and size of openings associated with each pad or strip can vary. It will be appreciated that the number of switches is limited only by the size of the wafer, the opening diameter and the spacing. It will be further appreciated that when a large metal debris particle (or particles) is (are) trapped by the device, a number of switches will be activated simultaneously.

It will also be appreciated that the wafer can be coupled to a programmable device such as a computer in which each switch on the wafer is scanned sequentially either separately or collectively to derive information on the size and quantity of any conducting metal particles arriving on the wafer.

The output of the computer or programmable device can be coupled to a suitable display giving visual, digital or hard print-out information on number, size and position of the particles on the grid means and/or rate of collection or time between capture etc.

The device could also be used to provide audible warning signals or to interact with machinery generating the particles.

Many other modifications and variations may be made in the apparatus hereinbefore described, by those having experience in this technology, without departing from the concept of the present invention. Accordingly, it should be clearly understood that the apparatus depicted in the accompanying drawings and referred to in the foregoing description are illustrative only and are not intended as limitations on the scope of the invention.

What is claimed is:

1. An apparatus for detecting conductive metal debris particles in a fluid flowing in machinery, comprising:
an electrically insulating member having a first and second side interposed in such flowing fluid with such flowing fluid directed towards said first side of said member, a plurality of first electrically conductive means disposed on said first side of said member, a plurality of second electrically conductive means disposed on said first side of said member, a plurality of third electrically conductive means disposed on said second side of said member, a plurality of first openings through said member sized to allow passage of such fluid therethrough while preventing the passage therethrough of any such particles of at least a preselected size and disposed adjacent said first and second conductive means to provide at least a portion of said first and second conductive means at the periphery of each of said first openings, a plurality of second openings through said member sized to allow passage of such fluid therethrough and disposed to provide direct electrical interconnection between each of said second conductive means and each of said third conductive means through said second openings, and circuit means electrically interconnected with each of said plurality of said first means and each of said plurality of said third means to provide a signal when such a particle of said at least a preselected size is trapped in or across any of said first openings.

2. The apparatus as claimed in claim 1, wherein said first electrically conductive means are strip contacts.

3. The apparatus as claimed in claim 2, wherein said strip contacts are copper tracks.

4. The apparatus as claimed in claim 1, wherein said second electrically conductive means are pads.

5. The apparatus as claimed in claim 1, wherein said third electrically conductive means are connecting strips.

6. The apparatus as claimed in claim 1, wherein the said first openings are unplated.

7. The apparatus as claimed in claim 1, wherein said second openings are through-plated to provide electric contact between said second electrically conductive means and said third electrically conductive means.

8. The apparatus as claimed in claim 1, wherein said openings are arranged in spaced rows.

9. The apparatus as claimed in claim 1, wherein said insulating member comprises a perforated wafer.

10. The apparatus as claimed in claim 1, wherein said insulating member is mounted perpendicular to the flow direction of the fluid.

11. The apparatus as claimed in claim 1, wherein said circuit means includes an alarm.

12. The apparatus as claimed in claim 1, wherein said circuit means includes a means for switching off such machinery.

13. The apparatus as claimed in claim 1, wherein said circuit means includes a computer means to determine information on size and quantity of debris as such debris is collected on said first side of said member.

* * * * *